(12) United States Patent
Biem et al.

(10) Patent No.: US 10,395,004 B2
(45) Date of Patent: *Aug. 27, 2019

(54) HYPOTHESIS-DRIVEN, REAL-TIME ANALYSIS OF PHYSIOLOGICAL DATA STREAMS USING TEXTUAL REPRESENTATIONS

(71) Applicant: INTERNATIONAL BUSINESS MACHINES CORPORATION, Armonk, NY (US)

(72) Inventors: Alain E. Biem, Yorktown Heights, NY (US); Timothy R. Dinger, Croton-on-Hudson, NY (US); Nagui Halim, Yorktown Heights, NY (US); Gang Luo, Yorktown Heights, NY (US); Daby M. Sow, Croton-on-Hudson, NY (US); Deepak S. Turaga, Elmsford, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 788 days.

This patent is subject to a terminal disclaimer.

(21) Appl. No.: 14/990,198

(22) Filed: Jan. 7, 2016

(65) Prior Publication Data

US 2016/0188812 A1 Jun. 30, 2016

Related U.S. Application Data

(63) Continuation of application No. 13/571,439, filed on Aug. 10, 2012, now abandoned, and a continuation of
(Continued)

(51) Int. Cl.
*G06F 16/245* (2019.01)
*G06N 5/02* (2006.01)
(Continued)

(52) U.S. Cl.
CPC ...... *G06F 19/324* (2013.01); *G06F 16/24568* (2019.01); *G06F 19/00* (2013.01); *G06N 5/02* (2013.01); *G16H 50/20* (2018.01)

(58) Field of Classification Search
CPC .. G06F 19/324; G06F 17/30516; G06F 19/00; G16H 50/20; G06N 5/02
See application file for complete search history.

(56) References Cited

U.S. PATENT DOCUMENTS 6,816,858 B1 * 11/2004 Coden ............... G06F 17/30855
386/241
7,269,516 B2 9/2007 Brunner et al.
(Continued)

OTHER PUBLICATIONS

Hunter, Jim, et al. "Using natural language generation technology to improve information flows in intensive care units." ECAI. 2008. (Year: 2008).*
(Continued)

*Primary Examiner* — Eric Nilsson
(74) *Attorney, Agent, or Firm* — Griffiths & Seaton PLLC

(57) ABSTRACT

A method of analyzing physiological data streams. According to the method, physiological data is received into a computerized machine. The physiological data comprises numerical data and medical symptoms of a patient. Features are extracted from the physiological data based on development of the physiological data over a period of time. The features are converted into a textual representation using natural language generation. Input terms for an information retrieval system operating on the computerized machine are automatically generated based on the features. The input terms are input to the information retrieval system. A corpus of data is automatically searched to retrieve results to the input terms using the information retrieval system.

20 Claims, 11 Drawing Sheets

Related U.S. Application Data application No. 13/570,680, filed on Aug. 9, 2012, now Pat. No. 9,292,576.

(51) Int. Cl.
| | |
|---|---|
| *G06N 20/00* | (2019.01) |
| *G06F 19/00* | (2018.01) |
| *G06F 16/2455* | (2019.01) |
| *G16H 50/20* | (2018.01) |

(56) References Cited

U.S. PATENT DOCUMENTS

| | | |
|---|---|---|
| 8,123,683 B2 | 2/2012 | Stupp et al. |
| 2005/0086045 A1 | 4/2005 | Murata |
| 2008/0222251 A1 | 9/2008 | Parthasarathy |
| 2008/0243542 A1 | 10/2008 | Hammond et al. |
| 2009/0088606 A1 | 4/2009 | Cuddihy et al. |
| 2010/0205006 A1 | 8/2010 | Bergh |
| 2011/0191270 A1 | 8/2011 | Peng et al. |
| 2011/0283287 A1 | 11/2011 | Ha |
| 2012/0078837 A1 | 3/2012 | Bagchi et al. |

OTHER PUBLICATIONS

Demner-Fushman, Dina, and Jimmy Lin. "Answering clinical questions with knowledge-based and statistical techniques." Computational Linguistics 33.1 (2007): 63-103. (Year: 2007).*

Hunter et al., "Using Natural Language Generation Technology to Improve Information Flows in Intensive Care Units ," Proc. 5th Conf. on Prestigious Applications of Intelligent Systems, 2008.

Sripada et al., "Summarizing Dive Computer Data: A Case Study in Integrating Textual and Graphical Presentations of Numerical Data," Proceedings of Workshop on Multimodal Output Generation, vol. CTIT Proceedings of the Workshop on Multimodal Output Generation, pp. 149-157,2007.

Sripada et al (2), "SUMTIME-METEO: Parallel Corpus of Naturally Occurring Forecast Texts and Weather Data," www.abdn.ac.uk/ncs/computing/research/nlg/projects/.../sumtime/.

Gibbon et al., "Introduction to Video Search Engines," ISBN: 978-3-540-79336-6, Spring 2008.

Kojima et al., "Generating Natural Language Description of Human Behavior From Video Images," Proceedings 15 Th International Conference on Pattern Recognition.

Bordawekar et al., "Analyzing Analytics Part 1: A survey of Business Analytics Models and Algorithms," IBM Research Report RC25186 (21107-029) Jul. 8, 2011.

Douglas E. Appelt, "FASTUS: A Finite-state Processor for Information Extraction from Real-world Text", 1993, pp. 1-8.

U.S. Appl. No. 13/750,680. Office Action Communication dated May 7, 2014. pp. 1-27.

U.S. Appl. No. 13/750,680. Office Action Communication dated Nov. 20, 2014 . pp. 1-34.

U.S. Appl. No. 13/750,680. Office Action Communication dated Jun. 3, 2015. pp. 1-22.

U.S. Appl. No. 13/571,439. Office Action Communication dated May 7, 2014. pp. 1-31.

U.S. Appl. No. 13/750,680. Office Action Communication dated Feb. 20, 2015. pp. 1-8.

U.S. Appl. No. 13/750,680. Office Action Communication dated Dec. 3, 2015. pp. 1-7.

Cao, Y. et al. "AskHERMES: An online question answering system for complex clinical questions." Journal of biomedical informatics vol. 44 No. 2 (2011). pp. 277-289.

Demner-Fushman, D. et al. "Answering clinical question with knowledge-based and statistical techniques." Computational Linguistics. vol. 33 No. 1 (2007). pp. 63-103.

* cited by examiner

HYPOTHESIS-DRIVEN, REAL-TIME ANALYSIS OF PHYSIOLOGICAL DATA STREAMS USING TEXTUAL REPRESENTATIONS

CROSS REFERENCE TO RELATED APPLICATION

This application claims the benefit under 35 U.S.C. § 120 as a continuation of U.S. application Ser. No. 13/570,680, filed Aug. 9, 2012, now U.S. Pat. No. 9,292,576, issued on Mar. 22, 2016, the entire teachings of which are incorporated herein by reference.

This invention was made with Government support under Contract No.: H98230-11-C-0276 awarded by the U.S. Department of Defense. The Government has certain rights in this invention.

BACKGROUND

The present disclosure relates to analysis of physiological data streams and in particular to real-time analysis of physiological data streams using textual representations.

While attending critically ill patients, each day a physician may be confronted with hundreds of variables. Clinical information systems capture physiological variables and device parameters online at least every minute. Some waveform signals such as electrocardiograms and electroencephalograms are sampled a few hundred to thousands of times per second. These physiological data samples are usually stored within the memory of the patient monitors for 72-96 hours and then discarded. Intensive Care Unit (ICU) patient records typically consist of paper notes, prepared manually, that represent 30 or 60 minutes' summaries of the enormous quantity of physiological data available. These summaries tend to be disjointed from other important data points captured in general medical records (e.g., laboratory test results, general hospital records). Physicians are required to integrate all these pieces of information manually to develop adequate representations of the state of their patients, and drive the appropriate treatment plan. Subtle yet clinically meaningful correlations are often buried within several multi-modal data streams, across long periods of time. The high dimension of this data and the time critical situations physicians are confronted with results in constant information overload. There is a lack of infrastructure support for the exploration and detection of such meaningful events in these data and as a result, medical care delivered in ICUs tends to be reactive. Physicians often react to significant events that have already occurred and affected the patient. Exploring these data points to identify the signature of such events as early as possible would allow proactive interventions before a complication negatively affects the patient.

SUMMARY

According to an embodiment herein, a method of analyzing physiological data is disclosed. According to the method, physiological data is received into a computerized machine. The physiological data comprises numerical data and medical symptoms of a patient. Features are extracted from the physiological data based on development of the physiological data over a period of time. The features are converted into a textual representation using natural language generation. Input terms for an information retrieval system operating on the computerized machine are automatically generated based on the features. The input terms are input to the information retrieval system. A corpus of data is automatically searched to retrieve results to the input terms using the information retrieval system.

According to another embodiment herein, another method is disclosed. According to the method, features are extracted from physiological data using a computerized device. The features are based on development of the physiological data over a period of time. The physiological data comprises numerical data and medical symptoms of a patient. At least one query based on the features is generated using the computerized device. Results to the at least one query are retrieved using a textual query engine operating on the computerized device. Hypotheses related to a medical condition of the patient are generated based on the results by comparing the results to the medical symptoms using the computerized device.

According to another embodiment herein, a method of performing real-time analysis of physiological data streams using textual representations is disclosed. The physiological data comprises numerical data and medical symptoms of a patient. According to the method, time series data is converted into text based on natural language generation using a computerized device. Textual queries are formulated from the text using the computerized device. The textual queries are output to external sources of unstructured data using the computerized device. Results of the textual queries are obtained from the external sources using the computerized device.

According to another embodiment herein, a computer system for exploration of time series physiological data streams is disclosed. The system includes an input/output port receiving physiological data. The physiological data comprises numerical data and medical symptoms of a patient. A processor is operatively connected to the input/output port. The processor automatically extracts features from the physiological data based on development of the physiological data over a period of time. The processor automatically converts the features into textual representation based on natural language generation. The processor automatically generates input terms based on the textual representation. The processor inputs the input terms to an information retrieval system. The processor automatically searches a corpus of data to retrieve results to the input terms using the information retrieval system.

According to another embodiment herein, a device for analyzing physiological data streams is disclosed. The device comprises a receiver receiving data from the physiological data streams. The data comprises information of a medical condition of a patient. The device comprises a question-answering system performing a plurality of question answering processes. A processor is connected to the question-answering system. The processor extracts a list of features from the data in the physiological data streams based on development of the physiological data over a period of time. The processor generates at least one query based on the list of features by converting the list of features to natural language. The processor presents the at least one query to the question-answering system. The processor receives at least one response to the at least one query. The processor develops a first hypothesis concerning a diagnosis of the medical condition of the patient based on the at least one response. The device includes a network interface that outputs the list of features to external sources separate from the question-answering system and receives at least one additional hypothesis concerning a diagnosis of the medical condition of the patient from the external sources. The processor recommends at least one of a treatment for the medical condition of the patient and at least one additional analysis based on the first hypothesis and the at least one additional hypothesis by comparing the first hypothesis and the at least one additional hypothesis to the medical symptoms.

According to another embodiment herein, a non-transitory computer readable storage medium readable by a computerized device is disclosed. The non-transitory computer readable storage medium stores instructions executable by the computerized device to perform a method. According to the method, physiological data is received. The physiological data comprises numerical data and medical symptoms of a patient. Features are extracted from the time series physiological data based on development of the physiological data over a period of time. The features are converted into a textual representation using natural language generation. Input terms for an information retrieval system operating on the computerized machine are automatically generated, based on the features. The input terms are input to the information retrieval system. A corpus of data is automatically searched to retrieve results to the input terms, using the information retrieval system. Hypotheses related to a medical condition of the patient are generated, based on the at least one answer by comparing the at least one answer to the medical symptoms.

BRIEF DESCRIPTION OF THE DRAWINGS

The embodiments herein will be better understood from the following detailed description with reference to the drawings, which are not necessarily drawing to scale and in which.

DETAILED DESCRIPTION

It will be readily understood that the embodiments of the present disclosure, as generally described and illustrated in the figures herein, may be arranged and designed in a wide variety of different configurations in addition to the embodiments described herein. Thus, the following detailed description of the embodiments, as represented in the figures, is not intended to limit the scope of the invention, as claimed, but is merely representative of selected embodiments. The following description is intended only by way of example, and simply illustrates certain embodiments of the invention, as claimed herein.

According to one embodiment, a novel method to dynamically discover new relationships in a multi-dimensional time series is disclosed. One aspect of this approach lies in the incorporation of unstructured textual data sources during the exploration process. In particular, according to embodiments herein, a disclosed method transforms times series data into textual summaries using natural language generation techniques. These summaries are then input to an automated information retrieval system, such as Google or Watson (Deep QA). Results, which may include ranking or importance scores, are returned. These results are then processed to formulate hypotheses that generate analytical patterns. The strength of these patterns is then assessed in real-time after being deployed and managed by a guidance and control system. The output of the guidance and control system is a dynamic set of flows optimized for the problem at hand.

In view of this, embodiments herein provide to the decision support systems the ability to evaluate a recommended action plan in the light of this unstructured information. More specifically, the methods and systems herein provide the ability to quickly identify, in a real-time setting, the relevant information from amongst the potentially huge amounts of unstructured information available.

Figure 1:
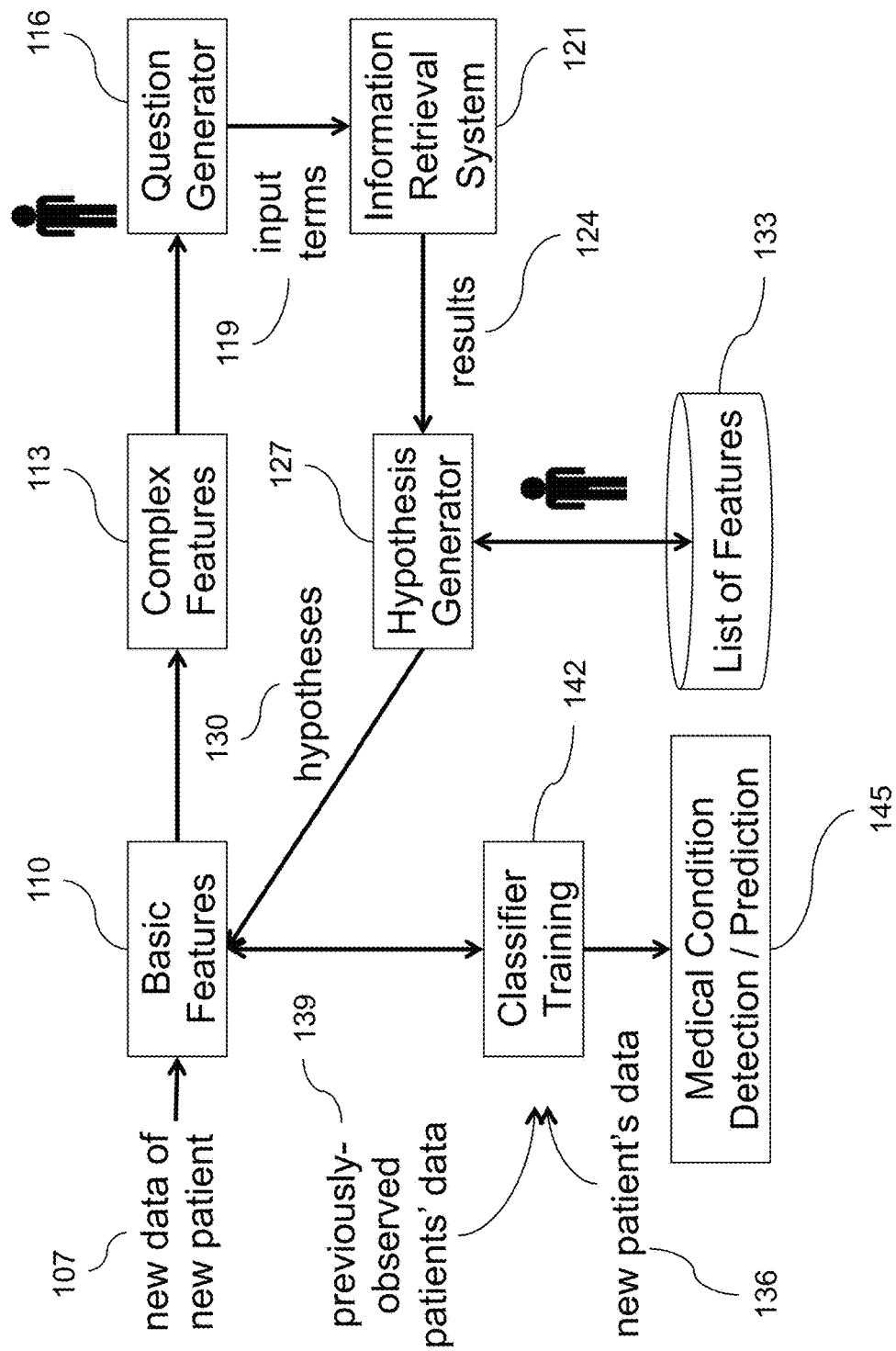
FIG. 1 is a schematic diagram illustrating process flow according to embodiments herein.

Referring now to the drawings, and more particularly to FIG. 1, new data of a new patient 107 may be input to a decision support system (described below). In an Intensive Care Unit (ICU), for example, there may be many physiological data streams, each having many features. Each feature is extracted from one or more physiological data streams and/or handled by one or more operators. The physiological data can come from any device that is monitoring a patient's health over time. It may include waveform signals such as electrocardiograms (ECG) and electroencephalograms (EEG) taken over a period of time. Numerical data may be extracted from such waveform signals and features may be extracted from the numerical data. Physiological data may further include patient reported symptoms, laboratory test results, general hospital records, etc. Typically, a medical health care provider may have a long, but possibly incomplete, list of features, and the system cannot compute all of the features simultaneously due to limited computing resources or incomplete medical knowledge. For example, for a new patient, basic features 110, such as increasing blood pressure and low heart rate, are extracted from the new data of a new patient 107. As used herein, a "feature" is a property of a phenomenon being observed. For example, from an ECG trace, the following information can be determined:

the heart rate
the heart rhythm
whether there are "conduction abnormalities" (abnormalities in how the electrical impulse spreads across the heart)
whether there has been a prior heart attack
whether there may be coronary artery disease
whether the heart muscle has become abnormally thickened All of these "features" are potentially important.

Basic features 110 are combined into complex features 113. Non-limiting examples of complex features 113 may include heart rate variability, SIRS (Systemic Inflammatory Response Syndrome) score, trend, etc. The "features" may include time series properties on uni-dimensional and multi-dimensional time series.

Other examples of complex features 113 may include such symptoms as Hyperglycemia (high blood sugar) at breakfast in combination with presence of glycosuria (glucose in urine), sometimes known as Dawn Effect in diabetes. Another example of complex features 113 may relate to a patient's response to hypertension, such as systolic and diastolic blood pressure may be increasing, steady, or decreasing; or the heart rate may be decreasing, steady, or increasing. Features may be numeric or structural, such as graphs or patterns. Identifying discriminating and independent features enables the system to provide accurate results. A health care provider may not know which features should be used for detection and/or prediction, but the health care provider can describe development of the features in natural language.

A question generator 116 uses natural language generation to provide input terms 119 from the basic features 110 or complex features 113. By natural language generation, we mean using technologies and methods for computer-based analysis and processing of natural language texts on the basis of linguistic models. The article by D. E. Appelt et al: "FASTUS: A Finite-State Processor for Information Extraction from Real-Word Text", Proceedings of IJCAI-93, Chambery, France, August 1993 p. 1172-1178 describes as an example a system for extraction of pre-specified information from "natural" i.e. not previously processed text, in this case news agency reports. In some embodiments, the natural language generation can be assisted by domain-specific and expert-specified rules. In other words, features are extracted from the time-series physiological data, and the features are converted to words to use as input terms 119 for an information retrieval system 121.

The input terms 119 are sent to an information retrieval system 121. According to embodiments herein, the information retrieval system 121 can be a search engine or a question-answering (QA) system. Knowledge is scattered in many places. Furthermore, much knowledge is available in textual form in both medical literature and clinical documents; however, text documents are typically unstructured. In some embodiments, the input terms 119 may be in the form of a natural language query to a QA system. The information retrieval system 121 searches a vast amount of data. Relevant results 124 from the information retrieval system 121 may include documents, web pages, and other text-based knowledge representations. In some embodiments, the results 124 may simply be an answer to a question. Historical data and medical condition labels from many previously-observed patients may be stored in a database for comparison of the various features.

The hypothesis generator 127 generates hypotheses 130 based on the results 124 retrieved from the information retrieval system 121. The process can be iterated to refine the hypotheses 130 using current and updated features. It is contemplated that the system described herein may use an external knowledge source 133 to assist in hypothesis generation and refinement. The list of features may be presented to outside experts in order to obtain additional opinions/knowledge information concerning the patient's features.

Unfortunately, there is a lack of consensus among health care providers on the best practice. Initially, analytics for a small number of initial features are deployed according to medical knowledge, which may generate relevant new features. A health care provider may then check whether some initially deployed features are irrelevant. As the results are obtained and hypotheses 130 are refined, the analytics for new features are deployed, and the analytics for irrelevant initial features are un-deployed.

Since every patient is different, the features may need to be personalized and adjusted based on trends or variation in time. According to embodiments herein, it is contemplated that the system will detect and/or predict the medical condition for the new patient using new data that will arrive in the future and old data that arrived in the past.

Using new patient's data 136 and previously-observed patients' data 139, a classifier 142 may be trained to detect and/or predict the medical condition 145. If the classification accuracy is low, the process can be iterated continually in order to refine the hypotheses 130.

In some embodiments, the generated textual representations can be displayed to a user to provide text-based visualization of queries, analytics, and results.

Figure 2:
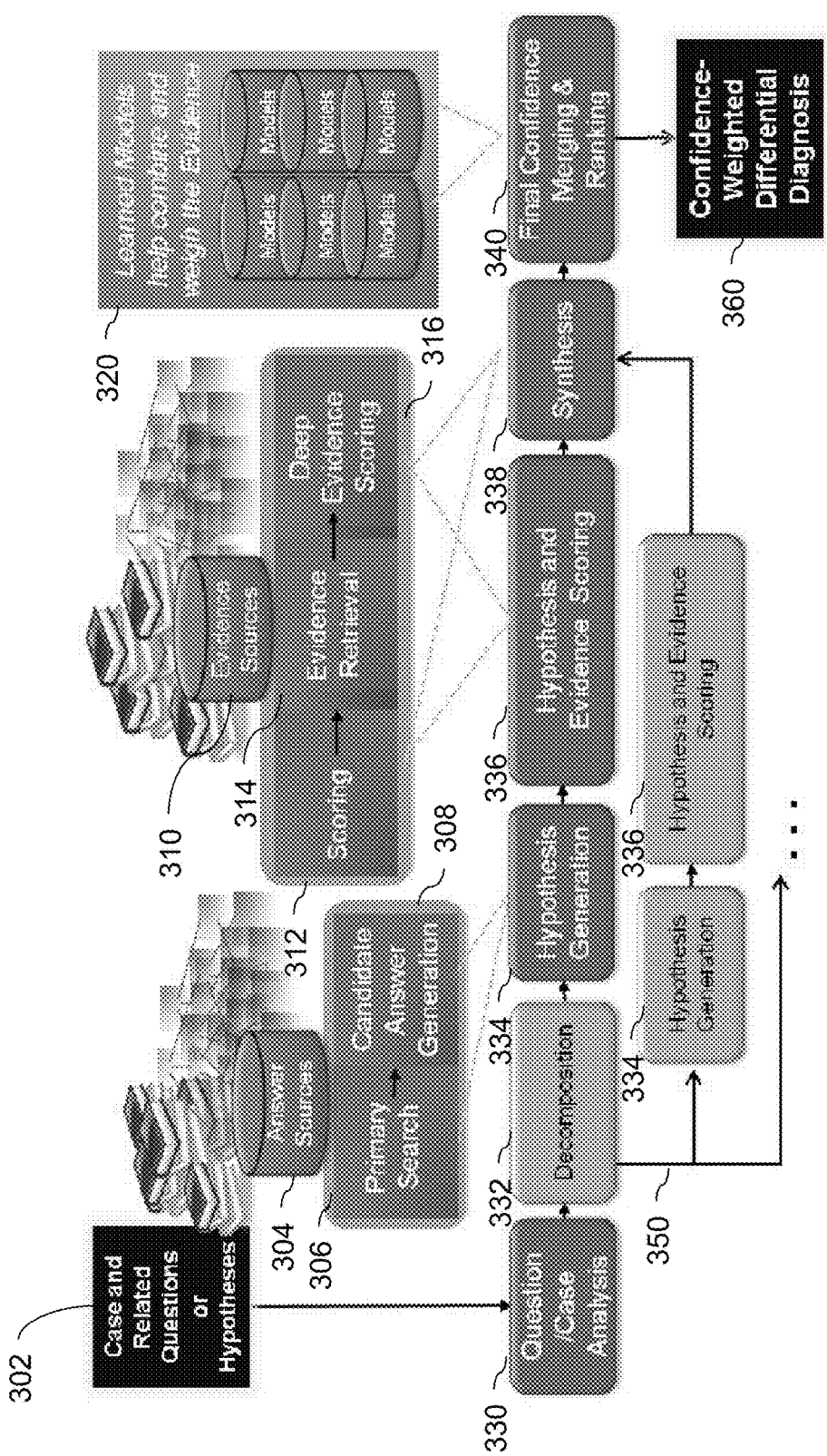
FIG. 2 is a schematic block diagram illustrating various aspects of embodiments herein.
Figure 3:
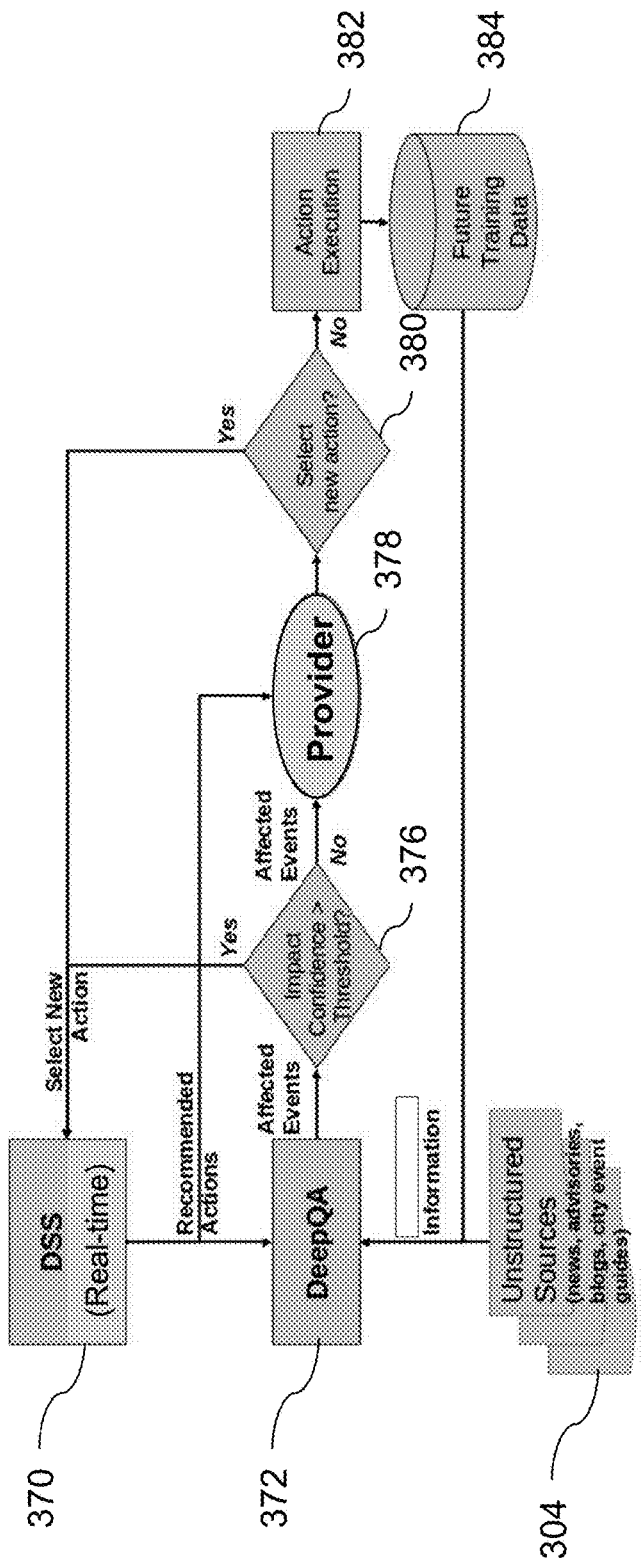
FIG. 3 is a schematic block diagram illustrating various aspects of embodiments herein.

Referring to FIGS. 2 and 3, a decision support system (DSS) 370 uses a database of structured and unstructured data 304 from a variety of unrelated sources to retrieve answers to queries and assign a relative confidence score based on the results. The methods and systems herein can execute queries to a question-answering system 372 with information extracted from the features using natural language questions. The methods and systems herein add to such a system by automatically generating questions and automatically retrieving answers to such questions. As shown in FIG. 2, the methods and systems herein use a Case and Related Question or Hypotheses phase 302 to generate a set of hypotheses (Hypothesis Generation 334) for answers to questions using unstructured information as evidence and associate a level of confidence with each hypothesis. More specifically, the Case and Related Question or Hypotheses phase 302 generates Questions and a Case Analysis 330, which is decomposed at Decomposition 332 into the Hypothesis Generation 334.

Thus, the systems and methods herein extract information from the basic features 110 and complex features 113. Using this information, the Hypothesis Generation 334 (sometimes referred to herein as the question generation phase) of the systems and methods herein issues a set of primary search queries 306 (sometimes referred to herein as questions) against answer sources from its corpus of structured and unstructured data 304. These answer sources from the unstructured data 304 could be websites, medical literature, clinical documents, and other sources of unstructured information.

Once the search results (sometimes referred to herein as retrieved results) are returned, a feature herein that is sometimes referred to as the Candidate Answer Generation phase 308 identifies a set of hypotheses from the unstructured search results. The Candidate Answer Generation phase 308 generates as many hypotheses as possible.

Once a broad set of hypotheses are generated, an operation referred to as the Hypothesis and Evidence Scoring 336 phase starts, where multiple scorers 312 assign features to each hypothesis. The following are some examples of scorers and features. A symptom scorer generates a feature based on the specific patient's presented data. A time-based scorer may reason about the trend of information over a period of time. A severity scorer may use information about the features to predict mortality, etc. Other scorers assign relative values from the text description of the features.

The scorers 312 used by embodiments herein range from simple heuristics rules using shallow lexical pattern matching to deeper semantic reasoning scorers supported by evidence sources and domain ontologies. As an example of a simple heuristic, the presence of certain keywords, or their combinations, in the feature description could be used by a scorer to assign a feature value. Similarly, a temporal scorer could use temporal concepts (e.g., DateTime, durations) and relations to estimate the time overlap. Additionally, heuristic-based scorers herein can directly evaluate the impact of the features on the recommended analytics. Further, the systems and methods herein can comprise learned models that learn the combined impact of the effect of such features on hypotheses and analytics during an off-line phase, as indicated by the item 320 in FIG. 2. Past instances of treatment actions that interacted with known features are used as off-line training data to develop the learned models. Results of action or inaction 382 can be recorded for training of future diagnoses 384.

As shown by item 350 in FIG. 2, the Decomposition 332 can result in many levels of Hypothesis Generation 334, Hypothesis and Evidence Scoring 336, etc., which are synthesized back together by the Synthesis phase 338. The learned models 320 are used to combine the features associated with each hypothesis during the Final Confidence Merging and Ranking phase 340 of the systems and methods herein. Multiple instance variants of the same features are also merged in this Final Confidence Merging and Ranking phase 340, pooling their feature values. This combination of weighted feature values results in an overall confidence of each hypothesis in its relevance to the treatment and/or analytics recommended by the DSS 370, as indicated by the Confidence-Weighted Differential Diagnosis 360, in FIG. 2. In addition to feature relevance, the learned models 320 may also estimate a confidence on the expected impact of the hypothesis on the treatment. Using the relevance and impact confidences, the hypotheses can be ranked from highest confidence to lowest.

As shown in FIG. 3, a health care provider 378 can be alerted to hypotheses with relatively high confidence in relevance and high confidence in impact (above a confidence threshold 376). The health care provider 378 can direct analytics or treatment be taken 380. In cases of high confidence in impact, the DSS 370 can be automatically triggered to re-run the hypothesis and/or analytics, taking into account the new information provided by the question-answering module (by operation of the decision box).

While many elements are mentioned above with respect to the question-answering system, those ordinarily skilled in the art would understand that each of the different elements discussed herein could be combined or separate (including the decision support system and the question-answering system, etc.). As shown in FIG. 2, with systems and methods herein, the health care provider 378 is given the option to drill down into each hypothesis and observe the various dimensions of evidence (used in the Evidence Retrieval 314 and Deep Evidence Scoring 316) used by the feature scorers (and the weights of such evidence) and further drill down to the actual evidence sources 310 found in the unstructured information. This allows the health care provider 378 to understand and evaluate the hypothesis more fully in order to make their own judgments as to relevance to and impact upon the proposed analytics. Thus, the systems and methods herein provide a different metric than those produced by the internal domain-specific plan generation tool, which allows a more thorough and relevant assessment about the likely benefit of the suggested analytics.

According to embodiments herein, the system uses natural language generation to convert time series data into text. The system can formulate textual queries to query external sources of unstructured data. The unstructured data is turned into useable knowledge/model. From this knowledge, the system dynamically generates hypotheses. The safer planet framework can be used to run new analytics in order to refine the hypotheses. The exploration results and retrieved knowledge is presented in textual form in order to seek expert feedback.

Figure 4:
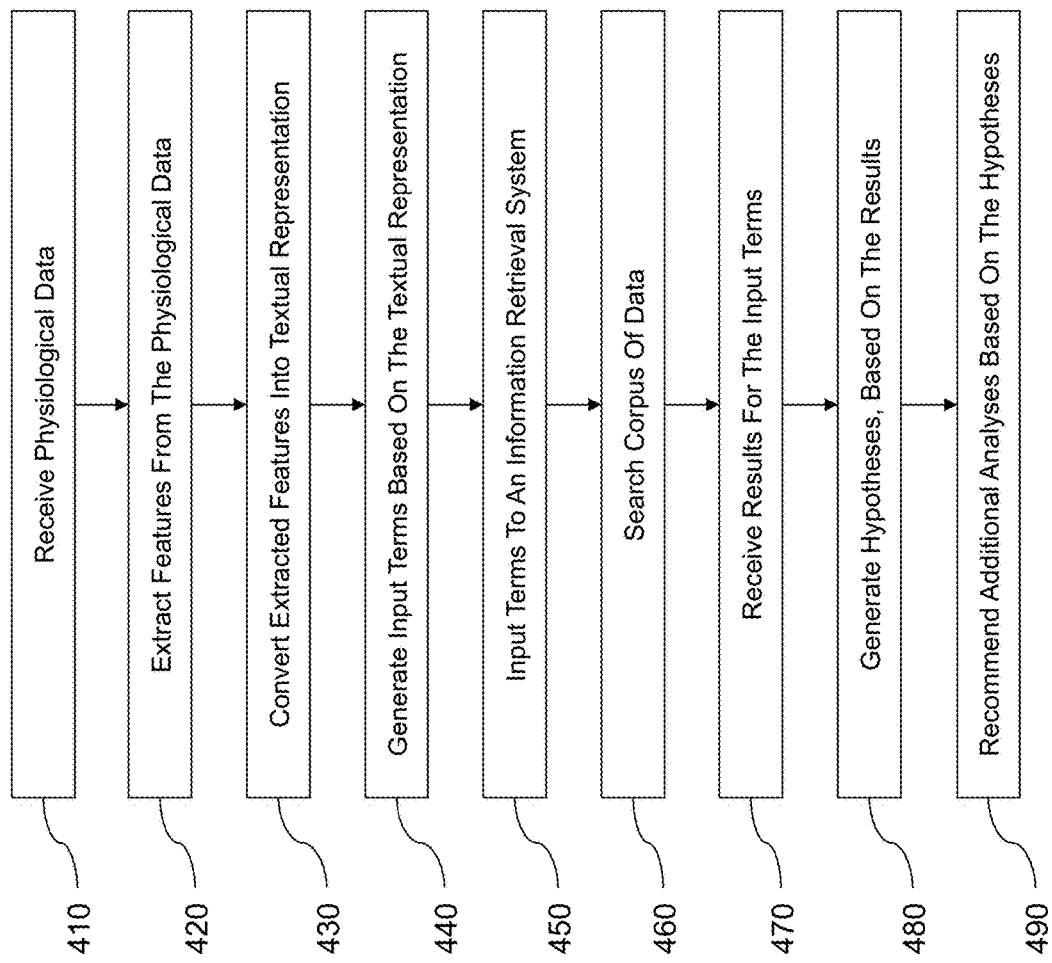
FIG. 4 is a flow diagram illustrating embodiments herein.

FIG. 4 is a flow diagram illustrating the processing flow of an exemplary method of analyzing physiological data according to embodiments herein. In item 410, the method begins by receiving time series physiological data into a computerized machine. Features are extracted from the time series physiological data, at 420. A feature is a property of a phenomenon being observed. The extracted features are converted into textual representation using natural language generation, at 430. In other words, the features are described in natural language as they develop. The process flow continues at 440 where questions, based on the textual representation, are automatically generated. The automatically generated questions are input to an information retrieval system operating on the computerized machine, at 450. At 460, a corpus of data is automatically searched to retrieve answers to the questions, using the information retrieval system. At 470, at least one answer to the question comprising information or a knowledge item is received on the computerized machine. Next in the process flow, hypotheses are generated, based on the at least one answer, at 480. The flow ends when one or more additional analyses are recommended based on the hypotheses, at 490. For example, if the ECG, as mentioned above, indicates a heart attack or possible coronary artery disease, further testing can be recommended to completely define the nature of the problem and decide on appropriate therapy.

Aspects of the present disclosure are described herein with reference to flowchart illustrations and/or block diagrams of methods, apparatus (systems), and computer program products according to various embodiments. It will be understood that each block of the flowchart illustrations and/or two-dimensional block diagrams, and combinations of blocks in the flowchart illustrations and/or block diagrams, can be implemented by computer program instructions. The computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

Figure 5:
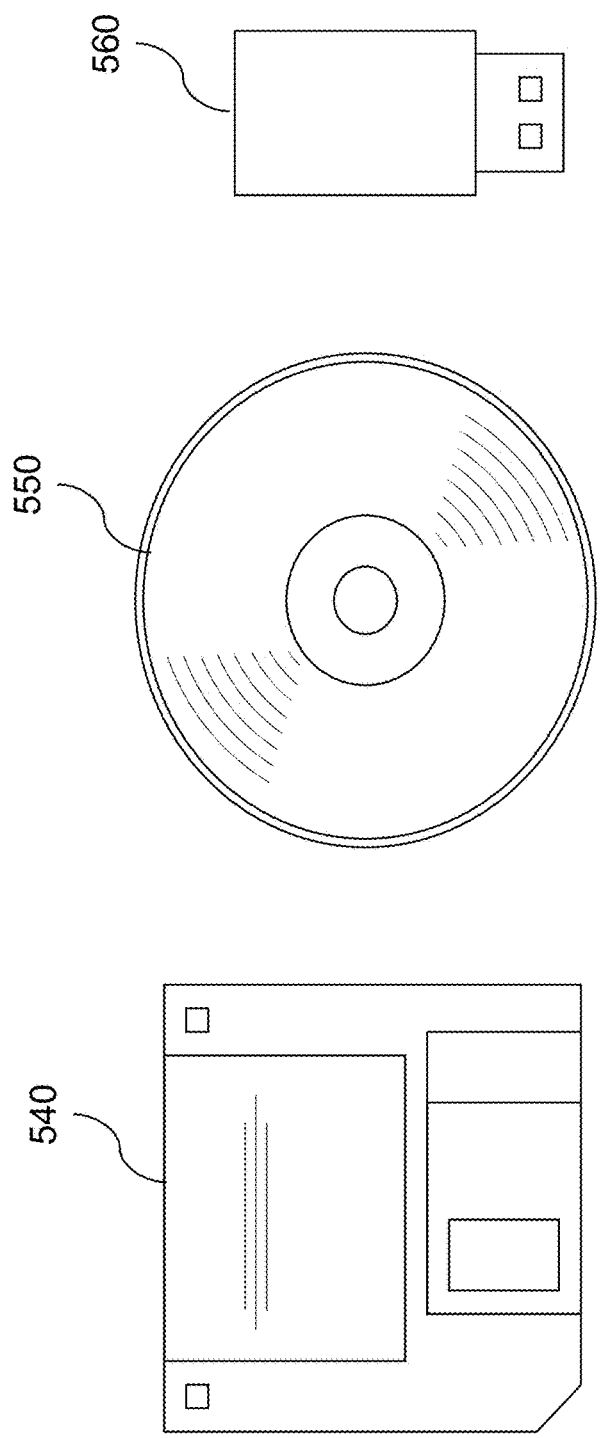
FIG. 5 is an illustration of articles of manufacture according to embodiments herein.

According to a further embodiment herein, an article of manufacture is provided that includes a computer readable medium having computer readable instructions embodied therein for performing the steps of the computer implemented methods, including but not limited to the method illustrated in FIG. 4. Any combination of one or more computer readable non-transitory medium(s) may be utilized. The computer readable medium may be a computer readable signal medium or a computer readable storage medium. The non-transitory computer storage medium stores instructions, and a processor executes the instructions to perform the methods described herein. A computer readable storage medium may be, for example, but not limited to, an electronic, magnetic, optical, electromagnetic, infrared, or semiconductor system, apparatus, or device, or any suitable combination of the foregoing. FIG. 5 illustrates exemplary articles of manufacture, such as, a magnetic storage device 540, a portable compact disc read only memory (CD-ROM) 550, and a "plug-and-play" memory device 560, like a USB flash drive. Any of these devices may have computer readable instructions for carrying out the steps of the methods described above with reference to FIG. 4.

The computer program instructions may be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

Furthermore, the computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

In case of implementing the embodiments herein by software and/or firmware, a program constituting the software may be installed into a computer with dedicated hardware, from a storage medium or a network, and the computer is capable of performing various functions if with various programs installed therein.

Figure 6:
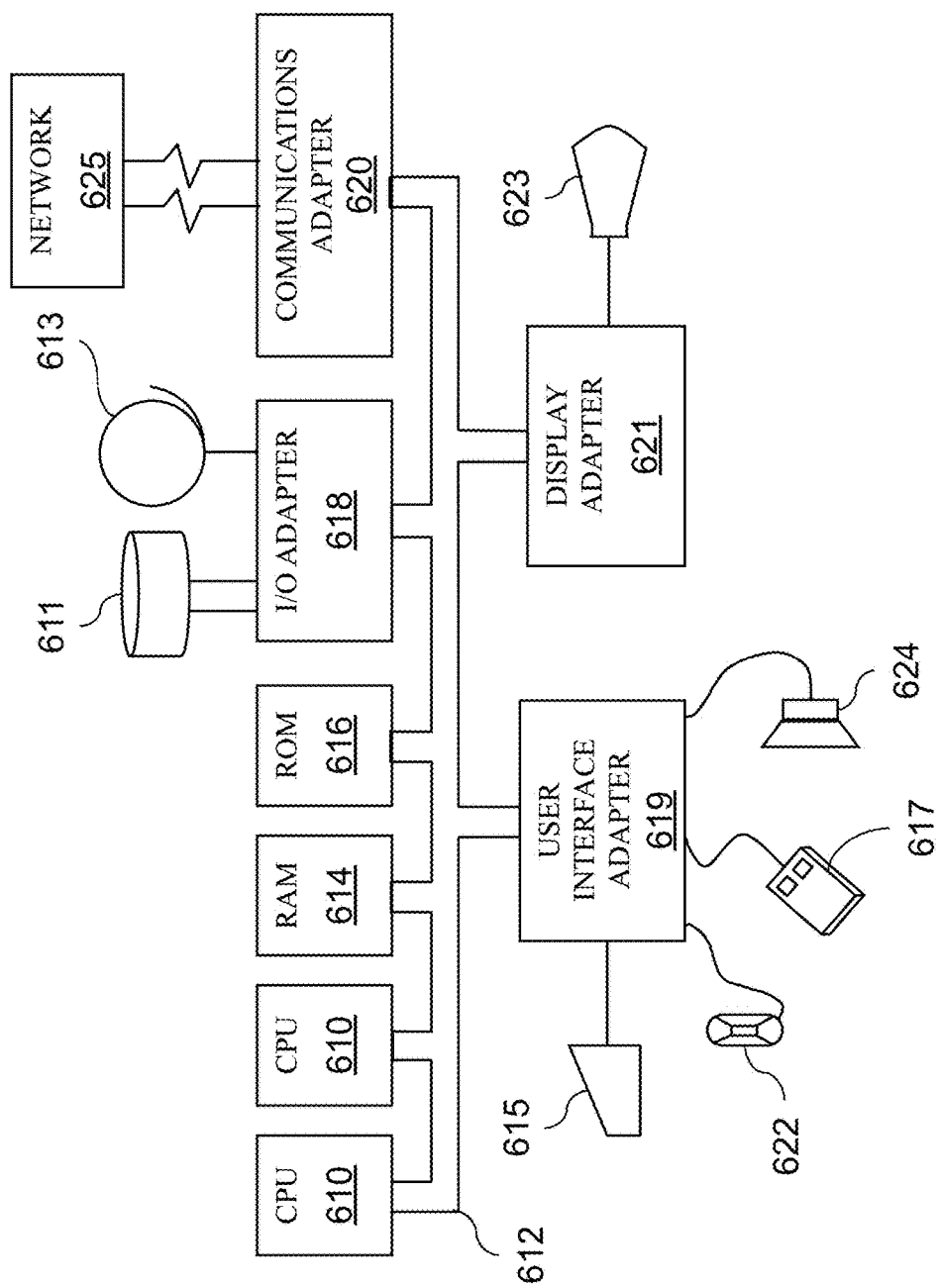
FIG. 6 is a schematic diagram of a hardware system according to embodiments herein.

A representative hardware environment for practicing the embodiments herein is depicted in FIG. 6. This schematic drawing illustrates a hardware configuration of an information handling/computer system in accordance with the embodiments herein. The system comprises at least one processor or central processing unit (CPU) 610. The CPUs 610 are interconnected via system bus 612 to various devices such as a random access memory (RAM) 614, read only memory (ROM) 616, and an input/output (I/O) adapter 618. The I/O adapter 618 can connect to peripheral devices, such as disk units 611 and tape drives 613, or other program storage devices that are readable by the system. The system can read the inventive instructions on the program storage devices and follow these instructions to execute the methodology of the embodiments herein.

In FIG. 6, CPUs 610 perform various processing based on a program stored in a Read Only Memory (ROM) 616 or a program loaded from a peripheral device, such as disk units 611 and tape drives 613 to a Random Access Memory (RAM) 614. In the RAM 614, required data when the CPU 610 performs the various processing or the like is also stored as necessary. The CPU 610, the ROM 616, and the RAM 614 are connected to one another via a bus 612. An input/output adapter 618 is also connected to the bus 612 to provide an input/output interface, as necessary. A removable medium, such as a magnetic disk, an optical disk, a magneto-optical disk, a semiconductor memory, or the like, is installed on the peripheral device, as necessary, so that a computer program read therefrom may be installed into the RAM 614, as necessary.

The system further includes a user interface adapter 619 that connects a keyboard 615, mouse 617, speaker 624, microphone 622, and/or other user interface devices such as a touch screen device (not shown) to the bus 612 to gather user input. Additionally, a communication adapter 620 including a network interface card such as a LAN card, a modem, or the like connects the bus 612 to a data processing network 625. The communication adapter 620 performs communication processing via a network such as the Internet. A display adapter 621 connects the bus 612 to a display device 623, which may be embodied as an output device such as a monitor (such as a Cathode Ray Tube (CRT), a Liquid Crystal Display (LCD), or the like), printer, or transmitter, for example.

In the case where the above-described series of processing is implemented with software, the program that constitutes the software may be installed from a network such as the Internet or a storage medium such as the removable medium.

Those skilled in the art would appreciate that the storage medium is not limited to the peripheral device having the program stored therein as illustrated in FIG. 5, which is distributed separately from the device for providing the program to the user. Examples of a removable medium include a magnetic disk (including a floppy disk), an optical disk (including a Compact Disk-Read Only Memory (CD-ROM) and a Digital Versatile Disk (DVD)), a magneto-optical disk (including a Mini-Disk (MD) (registered trademark)), and a semiconductor memory. Alternatively, the storage medium may be the ROM 616, a hard disk contained in the storage section 611, or the like, which has the program stored therein and is distributed to the user together with the device that contains them.

As will be appreciated by one skilled in the art, aspects of the systems and methods herein may be embodied as a system, method, or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable non-transitory medium(s) may be utilized. The computer readable medium may be a computer readable signal medium or a computer readable storage medium. The non-transitory computer storage medium stores instructions, and a processor executes the instructions to perform the methods described herein. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read only memory (ROM), an erasable programmable read only memory (EPROM or Flash memory), an optical fiber, a magnetic storage device 540 (FIG. 5), a portable compact disc read only memory (CD-ROM) 550, an optical storage device, a "plug-and-play" memory device 560, like a USB flash drive, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++, or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The flowchart and block diagrams in the Figures illustrate the architecture, functionality, and operation of possible implementations of systems, methods, and computer program products according to various embodiments herein. In this regard, each block in the flowchart or block diagrams may represent a module, segment, or portion of code, which comprises one or more executable instructions for implementing the specified logical function(s). It should also be noted that, in some alternative implementations, the functions noted in the block might occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Deployment types include loading directly in the client, server, and proxy computers via loading a storage medium such as a CD, DVD, etc. The process software may also be automatically or semi-automatically deployed into a computer system by sending the process software to a central server or a group of central servers. The process software is then downloaded into the client computers that will execute the process software. The process software is sent directly to the client system via e-mail. The process software is then either detached to a directory or loaded into a directory by a button on the e-mail that executes a program that detaches the process software into a directory. Alternatively, the process software is sent directly to a directory on the client computer hard drive. When there are proxy servers, the process will select the proxy server code, determine on which computers to place the proxy servers' code, transmit the proxy server code, and then install the proxy server code on the proxy computer. The process software will be transmitted to the proxy server, and then stored on the proxy server.

While it is understood that the process software may be deployed by manually loading directly in the client, server, and proxy computers via loading a storage medium such as a CD, DVD, etc., the process software may also be automatically or semi-automatically deployed into a computer system by sending the process software to a central server or a group of central servers. The process software is then downloaded into the client computers that will execute the process software. Alternatively, the process software is sent directly to the client system via e-mail. The process software is then either detached to a directory or loaded into a directory by a button on the e-mail that executes a program that detaches the process software into a directory. Another alternative is to send the process software directly to a directory on the client computer hard drive. When there are proxy servers, the process will select the proxy server code, determine on which computers to place the proxy servers' code, transmit the proxy server code, and then install the proxy server code on the proxy computer. The process software will be transmitted to the proxy server, and then stored on the proxy server.

Figure 7:
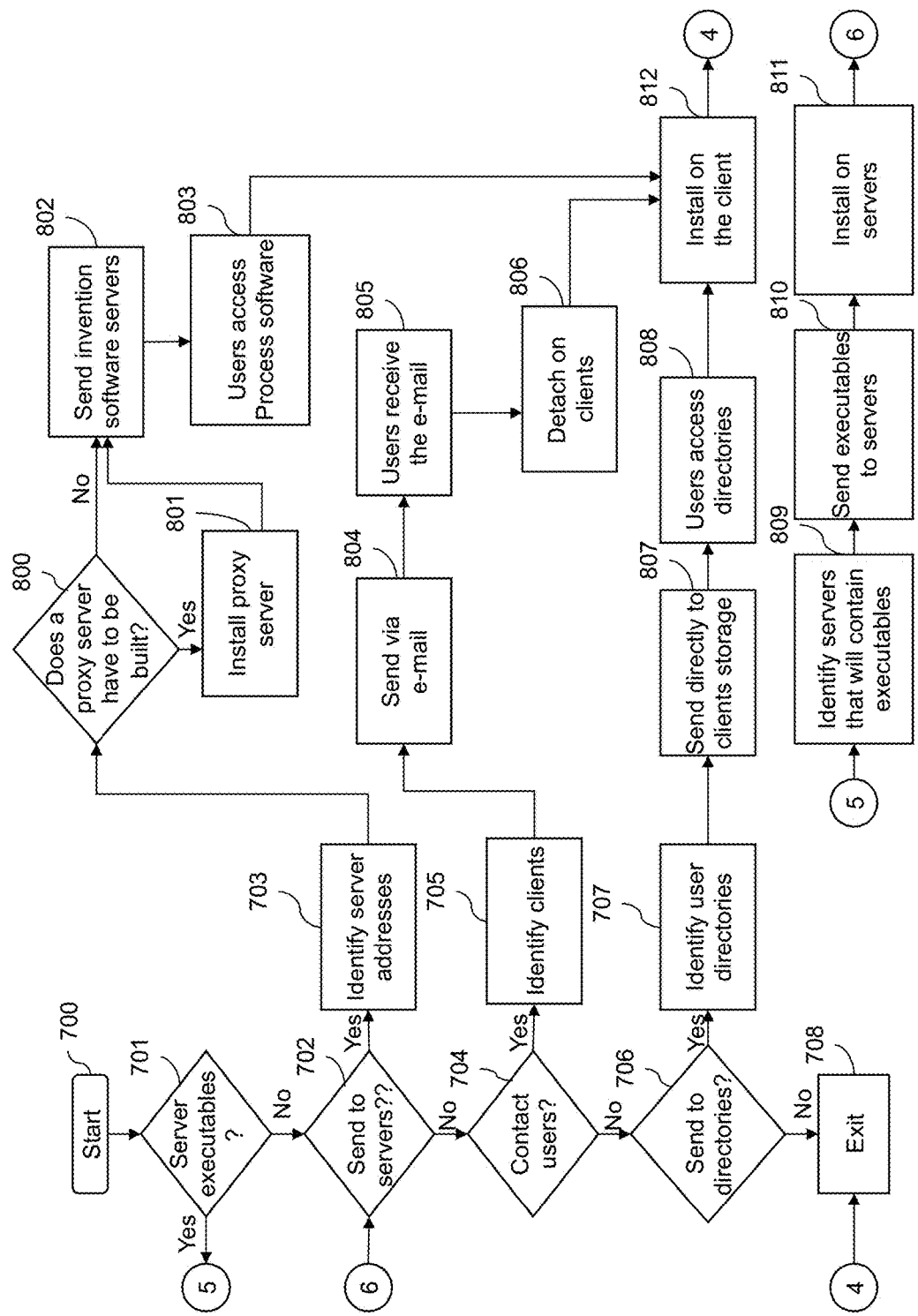
FIG. 7 is a schematic diagram of a deployment system according to embodiments herein.

In FIG. 7, step 700 begins the deployment of the process software. The first thing is to determine if there are any programs that will reside on a server or servers when the process software is executed 701. If this is the case, then the servers that will contain the executables are identified 809. The process software for the server or servers is transferred directly to the servers' storage via FTP or some other protocol, or by copying through the use of a shared file system 810. The process software is then installed on the servers 811.

Next, a determination is made on whether the process software is to be deployed by having users access the process software on a server or servers 702. If the users are to access the process software on servers, then the server addresses that will store the process software are identified 703.

A determination is made if a proxy server is to be built 800 to store the process software. A proxy server is a server that sits between a client application, such as a Web browser, and a real server. It intercepts all requests to the real server to see if it can fulfill the requests itself. If not, it forwards the request to the real server. The two primary benefits of a proxy server are to improve performance and to filter requests. If a proxy server is required, then the proxy server is installed 801. The process software is sent to the servers either via a protocol such as FTP or it is copied directly from the source files to the server files via file sharing 802. Another embodiment would be to send a transaction to the servers that contain the process software and have the server process the transaction, then receive and copy the process software to the server's file system. Once the process software is stored at the servers, the users, via their client computers, then access the process software on the servers and copy it to their client computer file systems 803. Another embodiment is to have the servers automatically copy the process software to each client and then run the installation program for the process software at each client computer. The users execute the program that installs the process software on their client computer 812, and then exit the process 708.

In step 704, a determination is made whether the process software is to be deployed by sending the process software to users via e-mail. The set of users where the process software will be deployed are identified together with the addresses of the user client computers 705. The process software is sent via e-mail 804 to each of the users' client computers. The users receive the e-mail 805 and then detach the process software from the e-mail to a directory on their client computers 806. The users execute the program that installs the process software on their client computer 812, and then exit the process 708.

Lastly, a determination is made on whether to the process software will be sent directly to user directories on their client computers 706. If so, the user directories are identified 707. The process software is transferred directly to the users' client computer directory 807. This can be done in several ways such as but not limited to sharing of the file system directories and then copying from the sender's file system to the recipient users' file system or alternatively using a transfer protocol such as File Transfer Protocol (FTP). The users access the directories on their client file systems in preparation for installing the process software 808. The users execute the program that installs the process software on their client computer 812, and then exit the process 708.

The process software is integrated into a client, server, and network environment by providing for the process software to coexist with applications, operating systems, and network operating systems software, and then installing the process software on the clients and servers in the environment where the process software will function.

The first step is to identify any software on the clients and servers including the network operating system where the process software will be deployed that are required by the process software or that work in conjunction with the process software. This includes the network operating system that is software that enhances a basic operating system by adding networking features.

Next, the software applications and version numbers will be identified and compared to the list of software applications and version numbers that have been tested to work with the process software. Those software applications that are missing or that do not match the correct version will be upgraded with the correct version numbers. Program instructions that pass parameters from the process software to the software applications will be checked to ensure the parameter lists match the parameter lists required by the process software. Conversely, parameters passed by the software applications to the process software will be checked to ensure the parameters match the parameters required by the process software. The client and server operating systems including the network operating systems will be identified and compared to the list of operating systems, version numbers, and network software that have been tested to work with the process software. Those operating systems, version numbers, and network software that do not match the list of tested operating systems and version numbers will be upgraded on the clients and servers to the required level.

After ensuring that the software, where the process software is to be deployed, is at the correct version level that has been tested to work with the process software, the integration is completed by installing the process software on the clients and servers.

Figure 8:
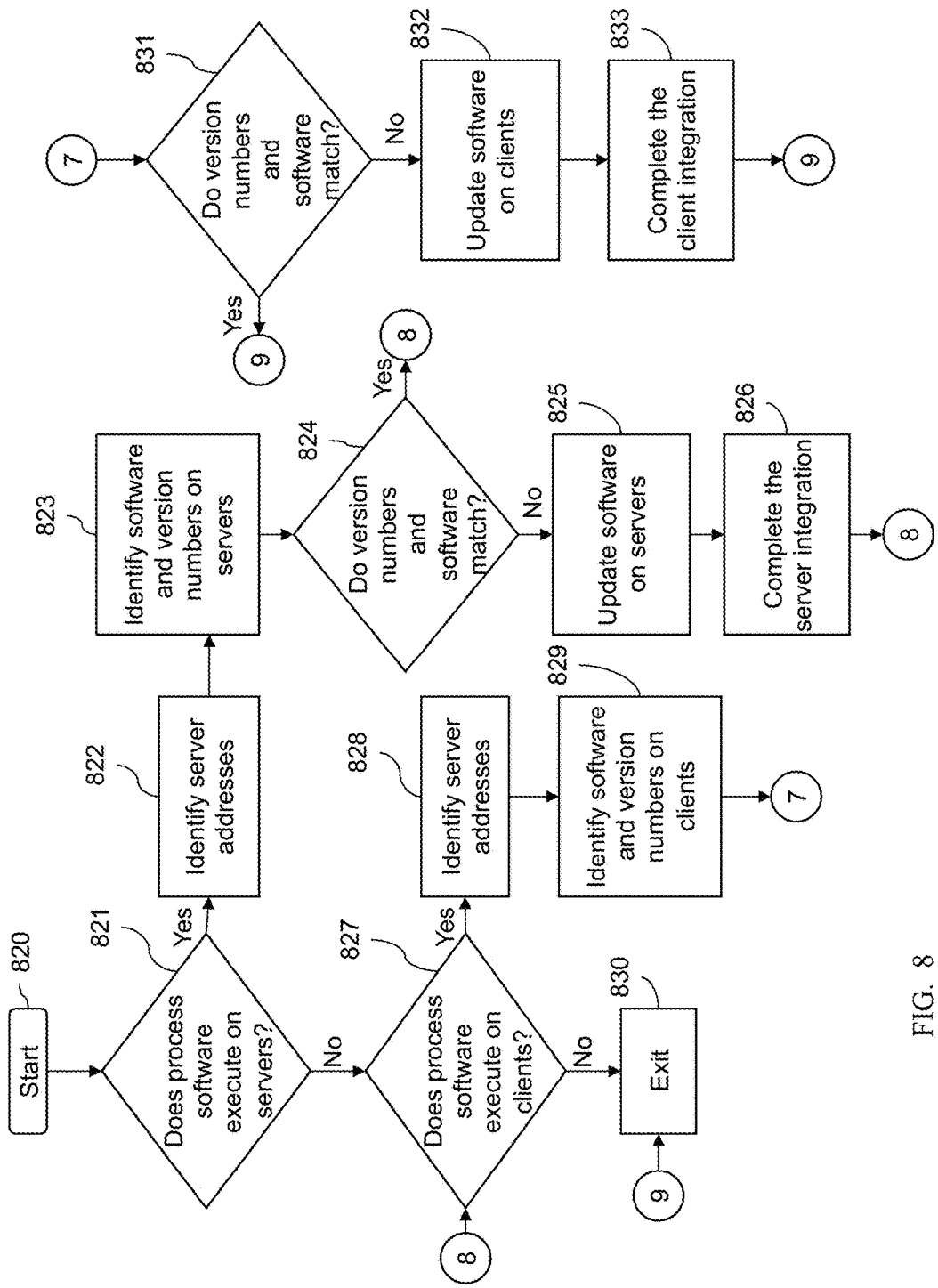
FIG. 8 is a schematic diagram of an integration system according to embodiments herein.

In FIG. 8, step 820 begins the integration of the process software. The first thing is to determine if there are any process software programs that will execute on a server or servers 821. If this is not the case, then integration proceeds to 827. If this is the case, then the server addresses are identified 822. The servers are checked to see if they contain software that includes the operating system (OS), applications, and network operating systems (NOS), together with their version numbers, that have been tested with the process software 823. The servers are also checked to determine if there is any missing software that is required by the process software 823.

A determination is made if the version numbers match the version numbers of OS, applications, and NOS that have been tested with the process software 824. If all of the versions match and there is no missing required software, the integration continues in 827.

If one or more of the version numbers do not match, then the unmatched versions are updated on the server or servers with the correct versions 825. Additionally, if there is missing required software, then it is updated on the server or servers 825. The server integration is completed by installing the process software 826.

Step 827, which follows either step 821, 824, or 826, determines if there are any programs of the process software that will execute on the clients. If no process software programs execute on the clients, the integration proceeds to 830 and exits. If this not the case, then the client addresses are identified 828.

The clients are checked to see if they contain software that includes the operating system (OS), applications, and network operating systems (NOS), together with their version numbers, that have been tested with the process software 829. The clients are also checked to determine if there is any missing software that is required by the process software 829.

A determination is made as to whether the version numbers match the version numbers of OS, applications, and NOS that have been tested with the process software 831. If all of the versions match and there is no missing required software, then the integration proceeds to 830 and exits.

If one or more of the version numbers do not match, then the unmatched versions are updated on the clients with the correct versions 832. In addition, if there is missing required software then it is updated on the clients 832. The client integration is completed by installing the process software on the clients 833. The integration proceeds to 830 and exits.

The process software can be stored on a shared file system accessible from one or more servers. The process software is executed via transactions that contain data and server processing requests that use CPU units on the accessed server. CPU units are units of time such as minutes, seconds, and hours on the central processor of the server. Additionally, the assessed server may make requests of other servers that require CPU units. CPU units are an example that represents one measurement of use. Other measurements of use include but are not limited to network bandwidth, memory usage, storage usage, packet transfers, complete transactions etc. When multiple customers use the same process software application, their transactions are differentiated by the parameters included in the transactions that identify the unique customer and the type of service for that customer. All of the CPU units and other measurements of use that are used for the services for each customer are recorded. When the number of transactions to any one server reaches a number that begins to affect the performance of that server, other servers are accessed to increase the capacity and to share the workload. Likewise, when other measurements of use such as network bandwidth, memory usage, storage usage, etc. approach a capacity so as to affect performance, additional network bandwidth, memory usage, storage etc. are added to share the workload. The measurements of use used for each service and customer are sent to a collecting server that sums the measurements of use for each customer for each service that was processed anywhere in the network of servers that provide the shared execution of the process software. The summed measurements of use units are periodically multiplied by unit costs and the resulting total process software application service costs are alternatively sent to the customer and/or indicated on a web site accessed by the customer, which then remits payment to the service provider. In another embodiment, the service provider requests payment directly from a customer account at a banking or financial institution. In another embodiment, if the service provider is also a customer of the customer that uses the process software application, the payment owed to the service provider is reconciled to the payment owed by the service provider to minimize the transfer of payments.

The process software is shared, simultaneously serving multiple customers in a flexible, automated fashion. It is standardized, requiring little customization, and it is scalable, providing capacity on demand in a pay-as-you-go model.

The process software can be stored on a shared file system accessible from one or more servers. The process software is executed via transactions that contain data and server processing requests that use CPU units on the accessed server. CPU units are units of time such as minutes, seconds, and hours on the central processor of the server. Additionally, the assessed server may make requests of other servers that require CPU units. CPU units are an example that represents one measurement of use. Other measurements of use include but are not limited to network bandwidth, memory usage, storage usage, packet transfers, complete transactions etc.

When multiple customers use the same process software application, their transactions are differentiated by the parameters included in the transactions that identify the unique customer and the type of service for that customer. All of the CPU units and other measurements of use that are used for the services for each customer are recorded. When the number of transactions to any one server reaches a number that begins to affect the performance of that server, other servers are accessed to increase the capacity and to share the workload. Likewise, when other measurements of use such as network bandwidth, memory usage, storage usage, etc. approach a capacity so as to affect performance, additional network bandwidth, memory usage, storage etc. are added to share the workload.

The measurements of use used for each service and customer are sent to a collecting server that sums the measurements of use for each customer for each service that was processed anywhere in the network of servers that provide the shared execution of the process software. The summed measurements of use units are periodically multiplied by unit costs and the resulting total process software application service costs are alternatively sent to the customer and/or indicated on a web site accessed by the customer, which then remits payment to the service provider.

In another embodiment, the service provider requests payment directly from a customer account at a banking or financial institution.

In another embodiment, if the service provider is also a customer of the customer that uses the process software application, the payment owed to the service provider is reconciled to the payment owed by the service provider to minimize the transfer of payments.

Figure 9:
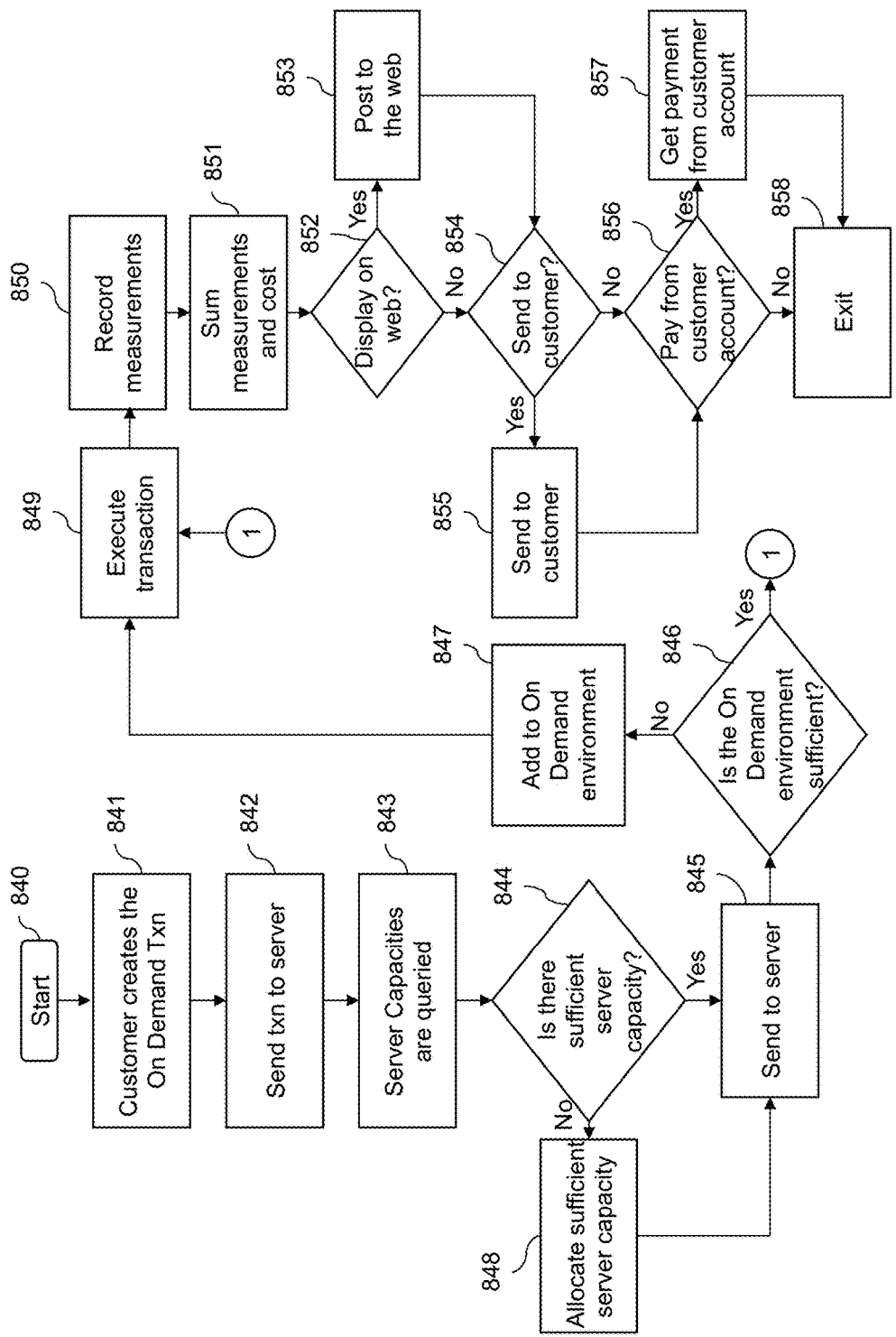
FIG. 9 is a schematic diagram of an on demand system according to embodiments herein.

In FIG. 9, step 840 begins the On Demand process. A transaction is created that contains the unique customer identification, the requested service type, and any service parameters that further specify the type of service 841. The transaction is then sent to the main server 842. In an On Demand environment, the main server can initially be the only server, then, as capacity is consumed, other servers are added to the On Demand environment.

The server central processing unit (CPU) capacities in the On Demand environment are queried 843. The CPU requirement of the transaction is estimated, then the servers' available CPU capacity in the On Demand environment are compared to the transaction CPU requirement to see if there is sufficient CPU capacity available in any server to process the transaction 844. If there is not sufficient server CPU capacity available, then additional server CPU capacity is allocated to process the transaction 848. If there was already sufficient CPU capacity available, then the transaction is sent to a selected server 845.

Before executing the transaction, a check is made of the remaining On Demand environment to determine if the environment has sufficient available capacity for processing the transaction. This environment capacity consists of such things as, but not limited to, network bandwidth, processor memory, storage etc. 846. If there is not sufficient available capacity, then capacity will be added to the On Demand environment 847. Next, the required software to process the transaction is accessed, loaded into memory, then the transaction is executed 849.

The usage measurements are recorded 850. The usage measurements consist of the portions of those functions in the On Demand environment that are used to process the transaction. The usage of such functions as, but not limited to, network bandwidth, processor memory, storage, and CPU cycles are what is recorded. The usage measurements are summed, multiplied by unit costs, and then recorded as a charge to the requesting customer 851. If the customer has requested that the On Demand costs be posted to a web site 852, then they are posted 853.

If the customer has requested that the On Demand costs be sent via e-mail to a customer address 854, then they are sent 855. If the customer has requested that the On Demand costs be paid directly from a customer account 856, then payment is received directly from the customer account 857. The last step is to exit the On Demand process 858.

The process software may be deployed, accessed and executed through the use of a virtual private network (VPN), which is any combination of technologies that can be used to secure a connection through an otherwise unsecured or untrusted network. The use of VPNs is to improve security and for reduced operational costs. The VPN makes use of a public network, usually the Internet, to connect remote sites or users together. Instead of using a dedicated, real-world connection such as leased line, the VPN uses "virtual" connections routed through the Internet from the company's private network to the remote site or employee.

The process software may be deployed, accessed, and executed through either a remote-access or a site-to-site VPN. When using the remote-access VPNs, the process software is deployed, accessed, and executed via the secure, encrypted connections between a company's private network and remote users through a third-party service provider. The enterprise service provider (ESP) sets a network access server (NAS) and provides the remote users with desktop client software for their computers. The telecommuters can then dial a toll-free number or attach directly via a cable or DSL modem to reach the NAS and use their VPN client software to access the corporate network and to access, download, and execute the process software.

When using the site-to-site VPN, the process software is deployed, accessed, and executed through the use of dedicated equipment and large-scale encryption, which are used to connect a company's multiple fixed sites over a public network, such as the Internet.

The process software is transported over the VPN via tunneling, which is the process of placing an entire packet within another packet and sending it over a network. The protocol of the outer packet is understood by the network and both points, called tunnel interfaces, where the packet enters and exits the network.

Figure 10:
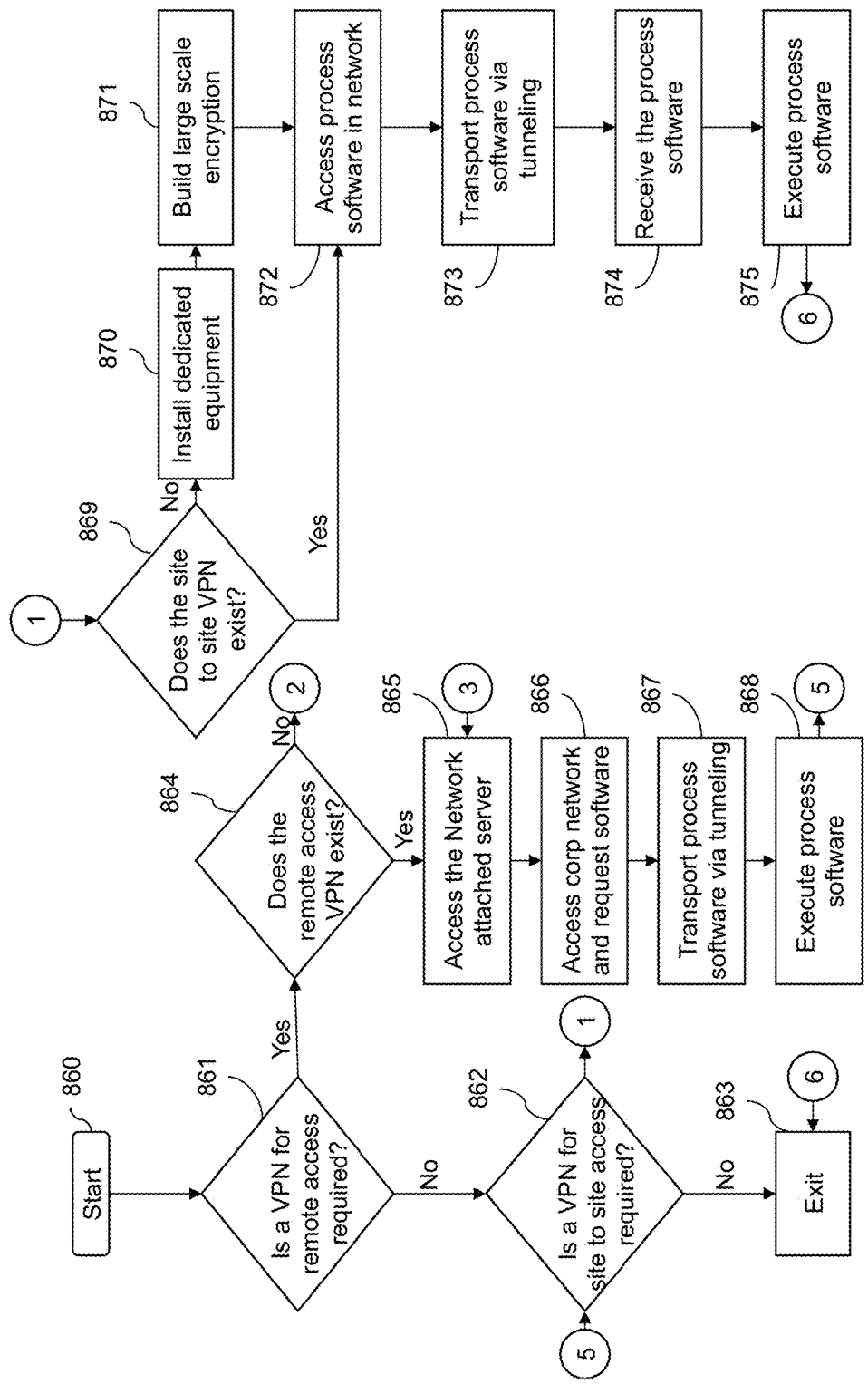
FIG. 10 is a schematic diagram of a virtual private network system according to embodiments herein.
Figure 11:
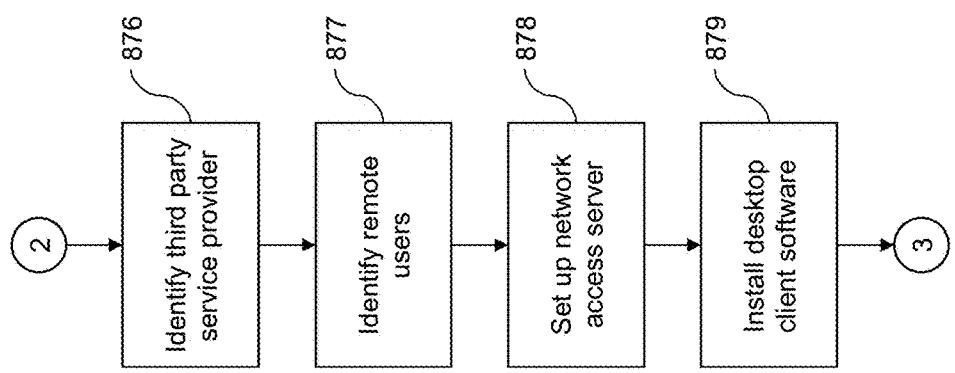
FIG. 11 is a schematic diagram of a virtual private network system according to embodiments herein.

In FIGS. 10 and 11, step 860 begins the Virtual Private Network (VPN) process. A determination is made to see if a VPN for remote access is required 861. If it is not required, then proceed to 862. If it is required, then determine if the remote access VPN exists 864.

If it does exist, then proceed to 865. Otherwise, identify the third party provider that will provide the secure, encrypted connections between the company's private network and the company's remote users 876. The company's remote users are identified 877. The third party provider then sets up a network access server (NAS) 878 that allows the remote users to dial a toll-free number or attach directly via a cable or DSL modem to access, download, and install the desktop client software for the remote-access VPN 879.

After the remote access VPN has been built, or if it been previously installed, the remote users can then access the process software by dialing into the NAS or attaching directly via a cable or DSL modem into the NAS 865. This allows entry into the corporate network where the process software is accessed 866. The process software is transported to the remote users' desktop over the network via tunneling. That is, the process software is divided into packets and each packet, including the data and protocol, is placed within another packet 867. When the process software arrives at the remote users' desktop, it is removed from the packets, reconstituted, and executed on the remote users' desktop 868.

A determination is made to see if a VPN for site-to-site access is required 862. If it is not required, then proceed to exit the process 863. Otherwise, determine if the site-to-site VPN exists 869. If it does exist, then proceed to 872. Otherwise, install the dedicated equipment required to establish a site-to-site VPN 870. Then build the large-scale encryption into the VPN 871.

After the site-to-site VPN has been built, or if it had been previously established, the users access the process software via the VPN 872. The process software is transported to the site users over the network via tunneling 873. That is, the process software is divided into packets and each packet, including the data and protocol, is placed within another packet 874. When the process software arrives at the remote users' desktop, it is removed from the packets, reconstituted, and executed on the site users' desktop 875. Proceed to exit the process 863.

The terminology used herein is for the purpose of describing particular embodiments only and is not intended to be limiting of this disclosure. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer system, comprising:
a decision support system, comprising:
an input/output port receiving physiological data associated with a patient having an unknown medical condition, said physiological data comprising streams of medical data obtained by monitoring said patient and medical symptoms reported by said patient; and
a processor operatively connected to said input/output port; and
an information retrieval system operatively connected to said decision support system, said information retrieval system comprising a corpus of data having structured and unstructured data in a relevant medical domain, said corpus of data being maintained in a separate database,
said processor:
automatically extracting numerical data from said physiological data based on development of said streams of medical data over a period of time,
automatically extracting features from said numerical data, said features comprising a property of said physiological data being observed,
automatically converting said features extracted from said physiological data into a textual representation using natural language generation, said natural language generation converting said features into words to use as input terms for said information retrieval system,
automatically generating a query for said information retrieval system using said input terms based on said textual representation and said medical symptoms reported by said patient, at least one said query being generated for each feature extracted from said physiological data, and
inputting said query to said information retrieval system,
said information retrieval system:
receiving said query, and
automatically searching said corpus of data and retrieving results to said query, said results indicating a possible medical condition of said patient in said period of time.

2. The computer system according to claim 1, said processor further
comparing said results obtained from said information retrieval system to said medical symptoms reported by said patient; and
generating hypotheses related to possible medical conditions of said patient based on said comparing said results obtained from said information retrieval system.

3. The computer system according to claim 2, said processor further recommending a medical test or analysis based on said hypotheses to confirm said possible medical conditions of said patient.

4. The computer system according to claim 2, said processor further
generating confidence scores for said hypotheses; and
ranking said hypotheses according to said confidence scores for said hypotheses and recommending additional analyses based on rank order of said hypotheses.

5. The computer system according to claim 2, said processor further
ranking said results obtained from said information retrieval system based on importance scores retrieved with said results;
formulating said hypotheses related to said possible medical conditions of said patient generating analytical patterns; and
identifying relationships among said physiological data based on said analytical patterns.

6. The computer system according to claim 5, further comprising:
a non-transitory storage medium, said processor storing a history of said results to said query, said hypotheses, and confidence scores for said hypotheses, in said non-transitory storage medium; and
said processor further correlating previously generated hypotheses and corresponding confidence scores stored in said non-transitory storage medium with at least one analysis based on said hypotheses.

7. The computer system according to claim 1, further comprising a user interface further outputting said results to said query and a link to said corpus of data indicating how said corpus of data contributed to said results.

8. The computer system according to claim 7, said user interface comprising a graphic user interface.

9. A device, comprising:
a receiver receiving physiological data associated with a patient having an unknown medical condition, said physiological data comprising streams of medical data obtained by monitoring said patient and medical symptoms reported by said patient;
a question-answering system operatively connected to said receiver, said question-answering system performing question answering processes, said question-answering system comprising a corpus of data comprising sources of structured and unstructured data in a relevant medical domain;
a processor connected to said question-answering system, said processor:
extracting numerical data from said physiological data based on development of said streams of medical data over a period of time;
extracting a list of features from said physiological data in said streams of medical data, each feature comprising a property of said physiological data being observed;
converting each feature extracted from said physiological data into a textual representation using natural language generation, said natural language generation converting said feature into words to use as input terms for said question-answering system;
generating queries for said question-answering system based on said list of features by converting said list of features to natural language, at least one query being generated for each feature;
presenting said queries to said question-answering system;
receiving at least one response to said queries;
comparing said at least one response to said medical symptoms reported by said patient; and
developing a first hypothesis concerning a diagnosis of a medical condition of said patient based on said at least one response; and
a network interface outputting said list of features to external sources separate from said question-answering system and receiving at least one additional hypothesis concerning a diagnosis of said medical condition of said patient from said external sources,
said processor recommending one of a treatment for said medical condition of said patient and at least one additional analysis based on said first hypothesis and said at least one additional hypothesis by comparing said first hypothesis and said at least one additional hypothesis to said medical symptoms.

10. The device according to claim 9, further comprising a user interface operatively connected to said processor, said user interface outputting at least one of said first hypothesis, said at least one additional hypothesis, said treatment for said medical condition of said patient, and said at least one additional analysis.

11. The device according to claim 9, said processor further generating confidence scores for said first hypothesis and said at least one additional hypothesis.

12. The device according to claim 11, said processor further ranking said at least one additional analysis according to said confidence scores for said first hypothesis and said at least one additional hypothesis.

13. The device according to claim 9, further comprising a non-transitory storage medium.

14. The device according to claim 13, said processor further storing a history of said at least one response to said queries, said first hypothesis, said at least one additional hypothesis, and confidence scores for said first hypothesis and said at least one additional hypothesis, in said non-transitory storage medium; and
said processor further correlating previously generated hypotheses and corresponding confidence scores stored in said non-transitory storage medium with said at least one additional analysis based on said first hypothesis and said at least one additional hypothesis.

15. A non-transitory computer readable storage medium readable by a computerized device, said non-transitory computer readable storage medium storing instructions executable by said computerized device to perform a method comprising:
receiving physiological data associated with a patient having an unknown medical condition, said physiological data comprising streams of medical data received over a period of time and medical symptoms reported by said patient;
extracting numerical data from said physiological data based on development of said streams of medical data over said period of time;
extracting features from said numerical data, said features comprising a property of said physiological data being observed;
converting said features into words based on natural language generation;
formulating textual queries from said words and said medical symptoms reported by said patient, at least one query being generated for each feature extracted from said numerical data;
outputting said textual queries to an external information retrieval system, said external information retrieval system having sources of data comprising structured and unstructured data in a relevant medical domain;

obtaining results of said textual queries from said external information retrieval system, said results indicating a possible medical condition of said patient based on said streams of medical data and said medical symptoms reported by said patient;

ranking said results based on importance scores retrieved with said results;

formulating hypotheses related to said possible medical condition of said patient to generate analytical patterns in said physiological data; and identifying relationships among said physiological data based on said analytical patterns.

16. The non-transitory computer readable storage medium according to claim 15, said method further comprising:

inputting said textual queries to said external information retrieval system;

searching a corpus of data with said information retrieval system to retrieve answers to said textual queries, said corpus of data comprising structured and unstructured data; and receiving at least one answer to said textual queries from said information retrieval system.

17. The non-transitory computer readable storage medium according to claim 15, said method further comprising:

dynamically generating hypotheses from said results of said textual queries based on comparing said results to said medical symptoms;

using a question answering system to run analytics to refine said hypotheses based on a self-generated confidence score for said hypotheses;

presenting results of said analytics and said results of said textual queries in textual form to an external expert; and obtaining feedback from said external expert.

18. The non-transitory computer readable storage medium according to claim 17, said using a question answering system to run analytics and refine said hypotheses further comprising:

generating new features from said physiological data;

verifying whether some initially deployed features are irrelevant; and using said new features and new physiological data to formulate textual queries to query said external information retrieval system.

19. The non-transitory computer readable storage medium according to claim 15, said method further comprising:

using features extracted from said physiological data and previously-observed data associated with said patient to train a classifier to detect or predict a medical condition of said patient.

20. The non-transitory computer readable storage medium according to claim 15, said method further comprising:

recommending a treatment for a medical condition of said patient or an additional analysis based on said hypotheses.

* * * * *